(12) United States Patent
Leibowitz

(10) Patent No.: US 11,109,903 B2
(45) Date of Patent: Sep. 7, 2021

(54) CANNULATED NAIL EXTRACTOR

(71) Applicant: Shukla Medical, St. Petersburg, FL (US)

(72) Inventor: Evan G. Leibowitz, Linden, NJ (US)

(73) Assignee: Shukla Medical, St. Petersburg, FL (US)

( * ) Notice: Subject to any disclaimer, the term of this patent is extended or adjusted under 35 U.S.C. 154(b) by 0 days.

(21) Appl. No.: 16/247,984

(22) Filed: Jan. 15, 2019

(65) Prior Publication Data
US 2020/0222098 A1 Jul. 16, 2020

(51) Int. Cl.
| | |
|---|---|
| *A61B 17/88* | (2006.01) |
| *A61B 17/86* | (2006.01) |
| *A61B 17/17* | (2006.01) |
| *A61B 17/74* | (2006.01) |
| A61B 17/72 | (2006.01) |

(52) U.S. Cl.
CPC ........ *A61B 17/864* (2013.01); *A61B 17/1725* (2013.01); *A61B 17/744* (2013.01); *A61B 17/1717* (2013.01); *A61B 17/7241* (2013.01); *A61B 17/7283* (2013.01)

(58) Field of Classification Search
CPC ....... A61F 2002/4619–462; A61B 17/92–921; A61B 17/72–7291
See application file for complete search history.

(56) References Cited

U.S. PATENT DOCUMENTS

| | | | | |
|---|---|---|---|---|
| 2,187,852 | A * | 1/1940 | Friddle | A61B 17/742 606/100 |
| 3,334,624 | A * | 8/1967 | Schneider | A61B 17/921 606/62 |
| 4,399,813 | A * | 8/1983 | Barber | A61B 17/1615 606/100 |
| 5,766,180 | A * | 6/1998 | Winquist | A61B 17/921 606/104 |
| 10,349,985 | B1 * | 7/2019 | Kriete | A61B 17/92 |
| 2005/0149051 | A1 * | 7/2005 | Hansson | A61B 17/92 606/104 |
| 2005/0228400 | A1 * | 10/2005 | Chao | A61B 17/7082 606/104 |
| 2006/0253120 | A1 * | 11/2006 | Anderson | A61B 17/808 606/86 R |
| 2007/0233154 | A1 * | 10/2007 | Kale | A61B 17/921 606/99 |

(Continued)

*Primary Examiner* — Eduardo C Robert
*Assistant Examiner* — Steven J Cotroneo
(74) *Attorney, Agent, or Firm* — Kim IP Law Group LLC

(57) ABSTRACT

A cannulated nail extractor including an extractor having a proximal end for connecting to an extraction device, a distal end opposite the proximal end, and a connector extending from the distal end. The cannulated nail extractor further includes an engagement wire having an enlarged proximal end configured to engage the extractor and an enlarged distal end configured to engage a distal end of the cannulated nail. The cannulated nail extractor further includes a positioning wire for insertion into the cannulated nail for urging the enlarged distal end of the engagement wire into engagement with the distal end of the cannulated nail, whereby exerting an extraction force on the extractor produces extraction force by engagement of the enlarged distal end of the engagement wire on the distally facing end of the cannulated nail.

34 Claims, 14 Drawing Sheets

(56) References Cited

U.S. PATENT DOCUMENTS

| | | | |
|---|---|---|---|
| 2010/0076438 A1* | 3/2010 | Correia | A61B 17/1675 606/79 |
| 2010/0087831 A1* | 4/2010 | Marx | A61B 17/92 606/104 |
| 2011/0034925 A1* | 2/2011 | Tipirneni | A61B 17/683 606/62 |
| 2012/0116466 A1* | 5/2012 | Dinville | A61B 17/7074 606/86 A |
| 2018/0206859 A1* | 7/2018 | Pendleton | A61B 17/1604 |
| 2019/0201008 A1* | 7/2019 | Sweitzer | A61B 17/92 |

\* cited by examiner

CANNULATED NAIL EXTRACTOR

The exemplary embodiments of present invention relate generally to a surgical extraction tool and, more specifically, to a tool for extracting a cannulated nail from a bone.

BACKGROUND OF THE DISCLOSURE

Fractures of long bones including, without limitation, the femur and tibia often require insertion of an intramedullary cannulated nail into the fractured bone and spanning the fracture site. The cannulated nail is typically anchored to the bone by a plurality of screws or similar fasteners located above and/or below the fracture site. The anchored cannulated nail spans and provides stability to the fractured area to promote healing thereof. When the bone is sufficiently healed and stable, the cannulated nail is removed from the bone, whereby the healing process proceeds to completion.

Oftentimes, however, during the bone healing process the cannulated nail becomes wedged in the bone or broken, thereby rendering removal of the cannulated nail difficult. While forceps or similar elongated clamping instruments may be able to grasp and remove an upper portion of a broken cannulated nail, such instruments are often ineffective in extracting tightly wedged cannulated nails or the lower portions of broken cannulated nails.

BRIEF SUMMARY OF THE DISCLOSURE

In accordance with an exemplary embodiment there is provided a cannulated nail extractor comprising an extractor that includes a proximal end for connecting to an extraction device, a distal end opposite the proximal end, and a connector extending from the distal end. The cannulated nail extractor further includes an engagement wire having an enlarged proximal end configured to engage the extractor and an enlarged distal end, and a positioning wire for insertion into the cannulated nail.

An aspect of the exemplary embodiment is that the extractor includes an elongated body, and/or a recessed seat for engaging the enlarged proximal end of the engagement wire. According to an aspect, the enlarged proximal end is nested within the extractor.

Another aspect of the exemplary embodiment is that the connector is releasably connected to the extractor including, without limitation, threadedly connected to the extractor. According to an aspect, the connector includes a through hole for the passage of the engagement wire therethrough, as well as a lateral slot for the passage of the engagement wire therethrough. The connector can further include a transverse slot to receive a spring clamp for releasably securing the connector to the extractor. According to an aspect, the connector includes a pair of opposing flat sides.

Another aspect of the exemplary embodiment is that the enlarged proximal end of the engagement wire is substantially bulbous-like, and/or includes a bearing attachable to the distal end of the extractor. According to an aspect, the engagement wire includes an elongated body and the enlarged distal end has a diameter larger than a diameter of the engagement wire body. The engagement wire can include a least one of a chamfer, round and/or step between a wire body of the engagement wire and the enlarged distal end. Another aspect of the exemplary embodiment is that the positioning wire has a constant diameter along substantially its entire length.

Another aspect of the exemplary embodiment is that an overall combined width of the positioning wire and enlarged distal end of the engagement wire is sufficiently larger than an overall inside diameter of a cannulated nail such that the overall combined width of the positioning wire and enlarged distal end of the engagement wire cannot pass through the cannulated nail. According to an aspect, an overall combined width of the positioning wire and a main wire body of the engagement wire is sufficiently smaller than an overall inside diameter of a cannulated nail such that the overall combined width of the positioning wire and the main wire body of the engagement wire can pass through the cannulated nail. In addition, an overall length of the engagement wire and positioning wire is sufficient to pass through an entirety of the cannulated nail.

In accordance with another exemplary embodiment of the subject disclosure there is provided a method for extracting a cannulated nail comprising, using the cannulated nail extractor in accordance with the first exemplary embodiment, inserting the engagement wire through the cannulated nail until the enlarged distal end passes through a bottom of the cannulated nail. The method further comprises inserting the positioning wire through the cannulated nail until a distal end of the positioning wire passes through the bottom of the cannulated nail and urges the enlarged distal end of the engagement wire into engagement with a distally facing end of the cannulated nail. The method further comprises exerting an extraction force on the extractor to produce extraction force by engagement of the enlarged distal end of the engagement wire on the distally facing end of the cannulated nail.

In accordance with the exemplary embodiments, there is provided a cannulated nail extractor and method for extracting a cannulated nail using the cannulated nail extractor that overcomes one more of the disadvantages of conventional devices. The engagement wire and the positioning wire are passed through the cannulated nail in sequence whereby the positioning wire urges the enlarged distal end of the engagement wire into engagement with a distally facing end of the cannulated nail. So constructed and arranged, an extraction force may be exerted on the extractor to produce extraction force by engagement of the enlarged distal end of the extraction wire on the distally facing end of the cannulated nail to effectively extract the nail from a bone in which the cannulated nail resides Other features and advantages of the subject disclosure will be apparent from the following more detail description of the exemplary embodiments.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the present disclosure, there are shown in the drawings exemplary embodiments. It should be understood, however, that the subject application is not limited to the precise arrangements and instrumentalities shown.

DETAILED DESCRIPTION OF THE DISCLOSURE

Figure 1:
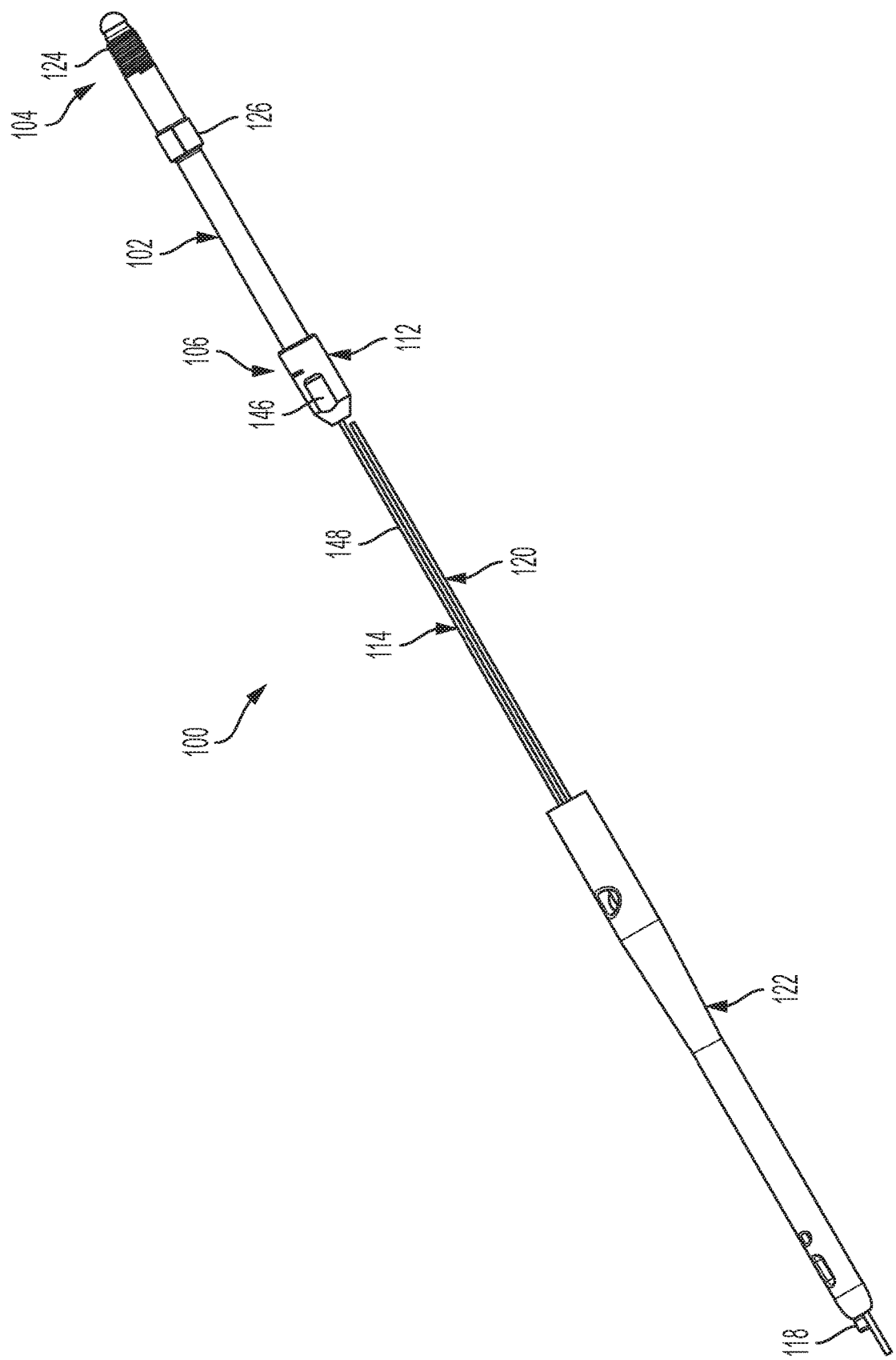
FIG. 1 is a perspective view of a cannulated nail extractor inserted in a cannulated nail in accordance with an exemplary embodiment of the subject disclosure.
Figure 2:
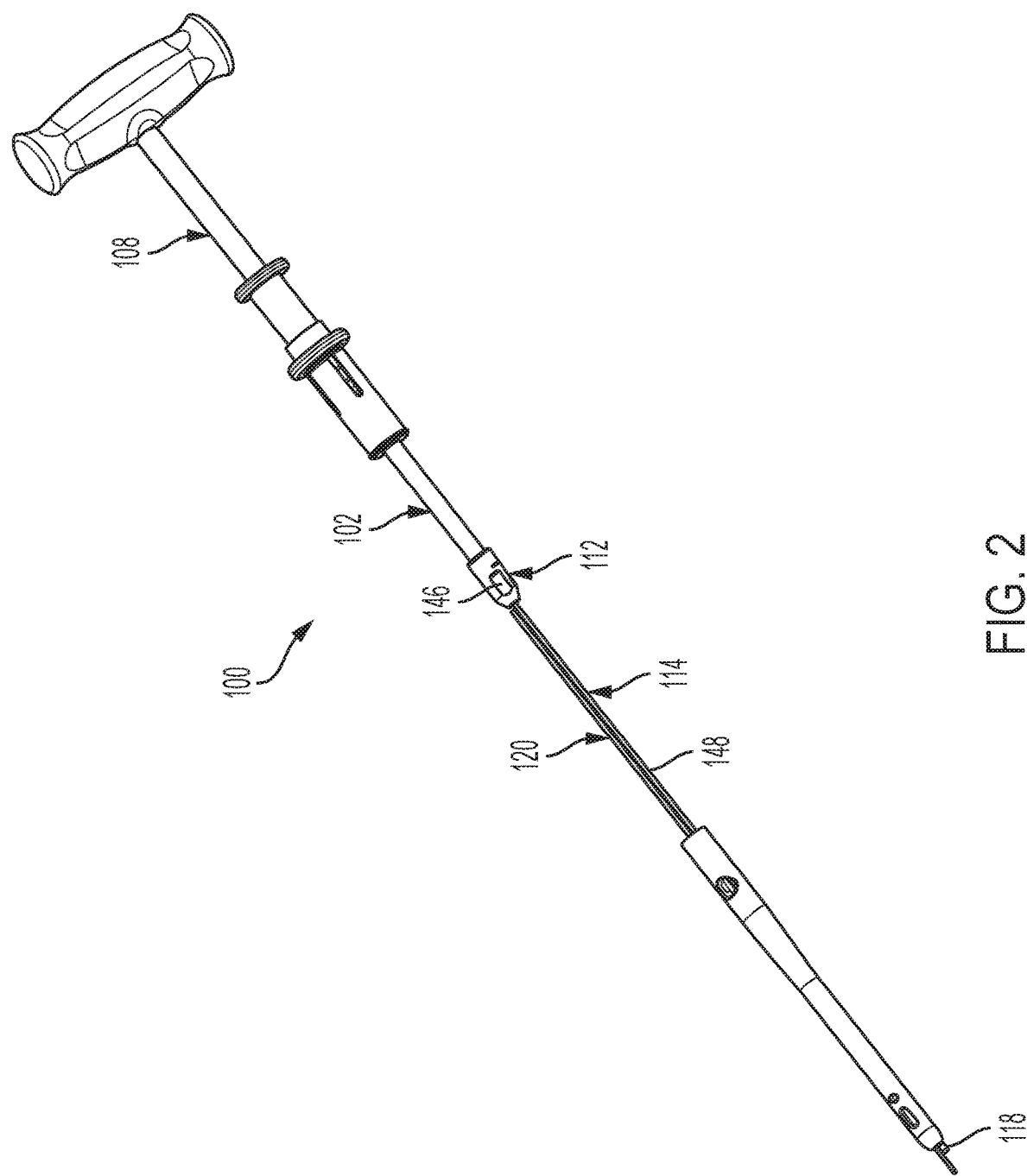
FIG. 2 is a perspective view of the cannulated nail extractor of FIG. 1 shown attached to a T-handle.
Figure 3:
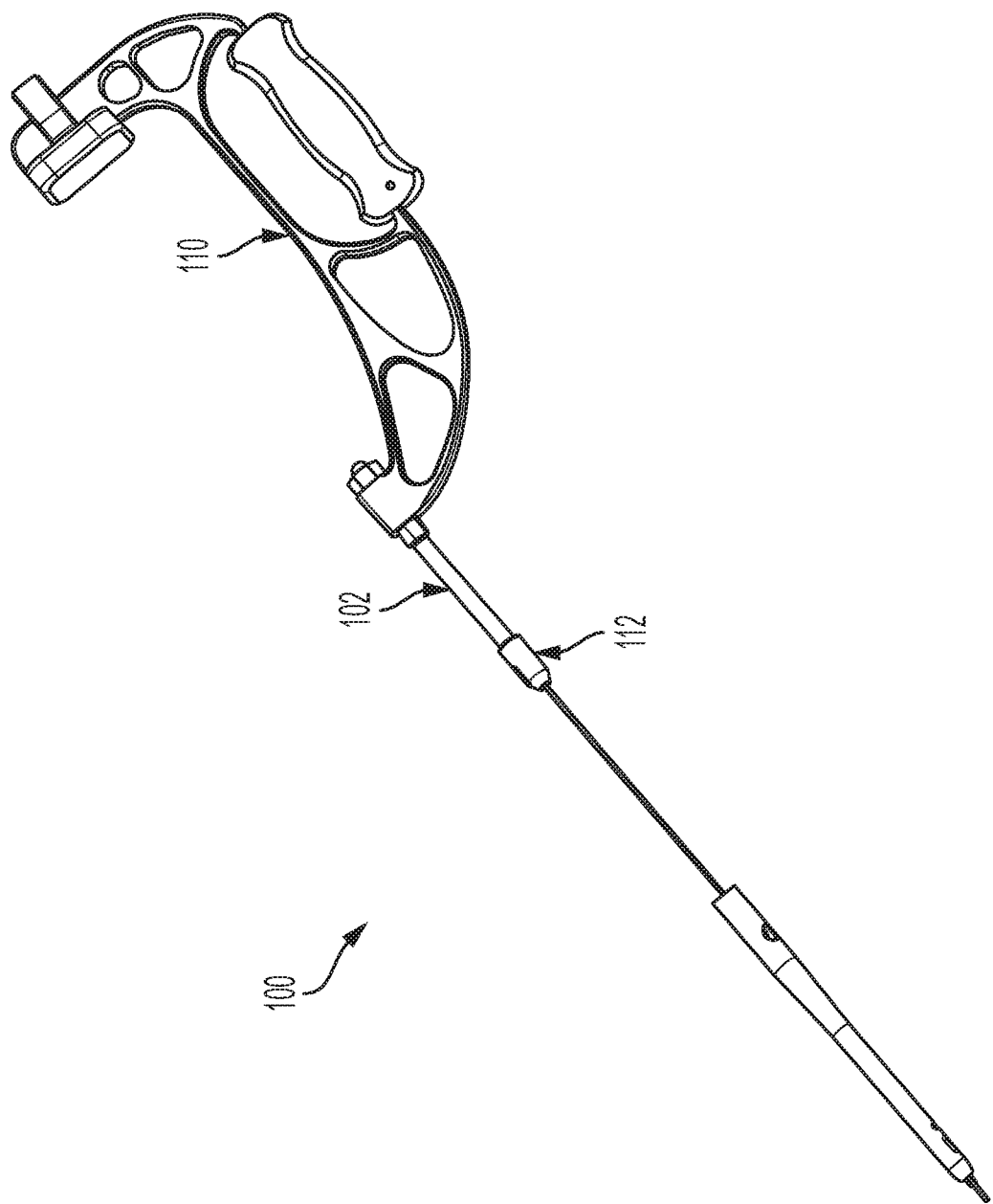
FIG. 3 is a perspective view of the cannulated nail extractor of FIG. 1 shown attached to a C-frame extraction device.
Figure 4:
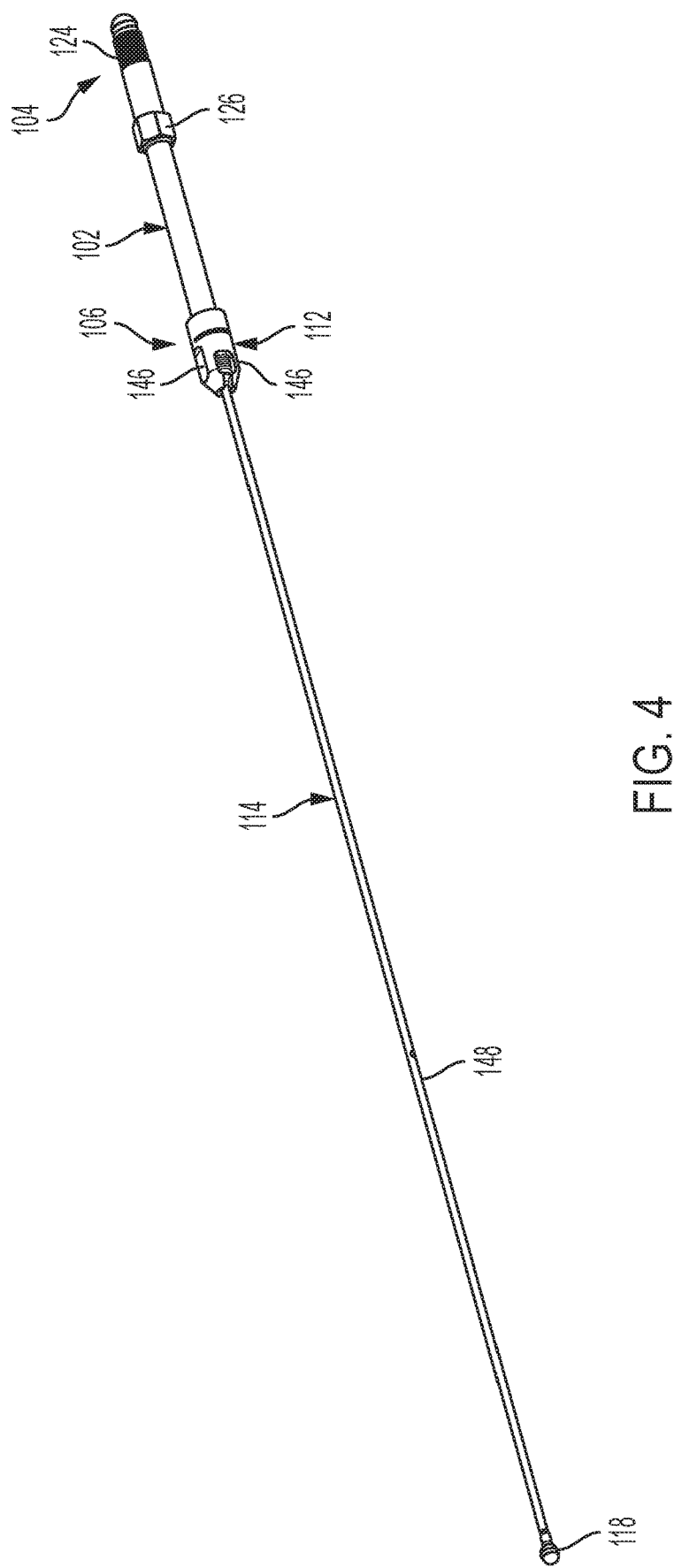
FIG. 4 is a perspective view of the cannulated nail extractor of FIG. 1 without a positioning wire.
Figure 5:
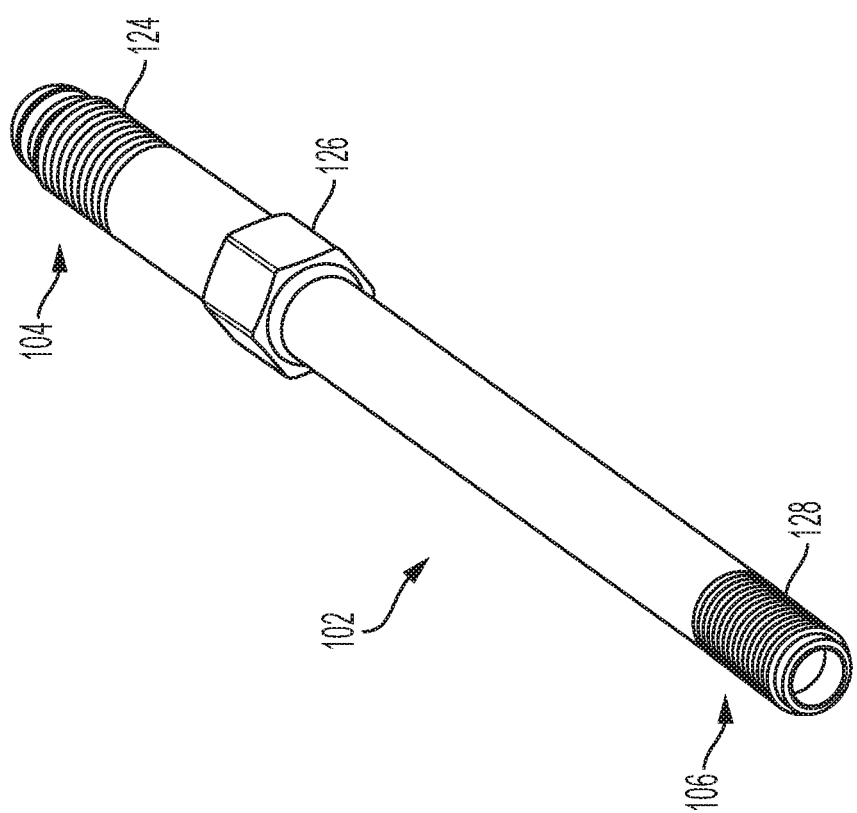
FIG. 5 is an enlarged perspective view of an extractor of the cannulated nail extractor of FIG. 1.
Figure 6:
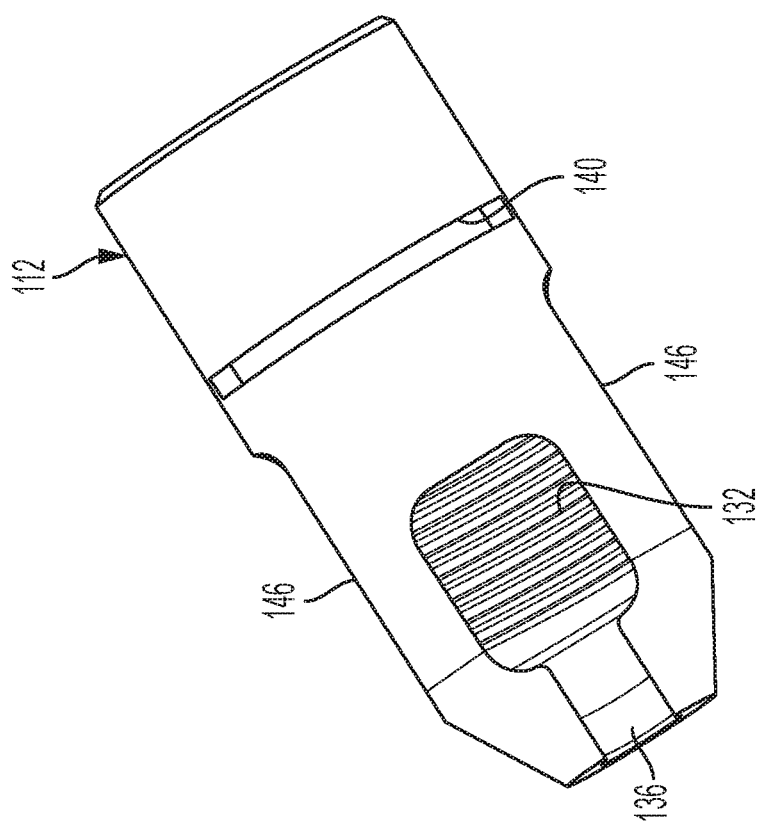
FIG. 6 is an enlarged perspective view of a connector of the cannulated nail extractor of FIG. 1.

Reference will now be made in detail to the various exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject application in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art.

Throughout the subject application, various aspects thereof can be presented in a range format. It should be understood that the description in range format is merely for convenience and brevity and should not be construed as an inflexible limitation on the scope of the subject disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments of the subject disclosure may be combined in any suitable manner in one or more embodiments. One skilled in the relevant art will recognize, in light of the description herein, that the subject disclosure can be practiced without one or more of the specific features or advantages of a particular exemplary embodiment. In other instances, additional features and advantages may be recognized in certain embodiments that may not be present in all exemplary embodiments of the present disclosure.

Referring now to the drawings, FIGS. 1-4 and 8 illustrate a cannulated nail extractor 100 in accordance with an exemplary embodiment of the present disclosure. The cannulated nail extractor 100 includes an extractor 102 having a proximal end 104 for connecting to an extraction device, and a distal end 106 opposite the proximal end. The extraction device connected to the proximal end 104 of the extractor may assume any suitable form of extraction device for exerting an extraction force including, without limitation, a T-handle 108 (FIG. 2) or a C-frame extraction device 110 (FIG. 3), the structures and functions of which are generally known and therefore a detailed description is not necessary for a complete understanding of the subject disclosure.

The cannulated nail extractor 100 further includes a connector 112 extending from the distal end 106 of the extractor 102, an engagement wire 114, and a positioning wire 120. The engagement wire 114 includes an enlarged proximal end 116 configured to engage the extractor 102 and an enlarged distal end 118. The positioning wire 120 is for insertion into the cannulated nail 122 for positioning of the engagement wire within the cannulated nail.

Figure 8:
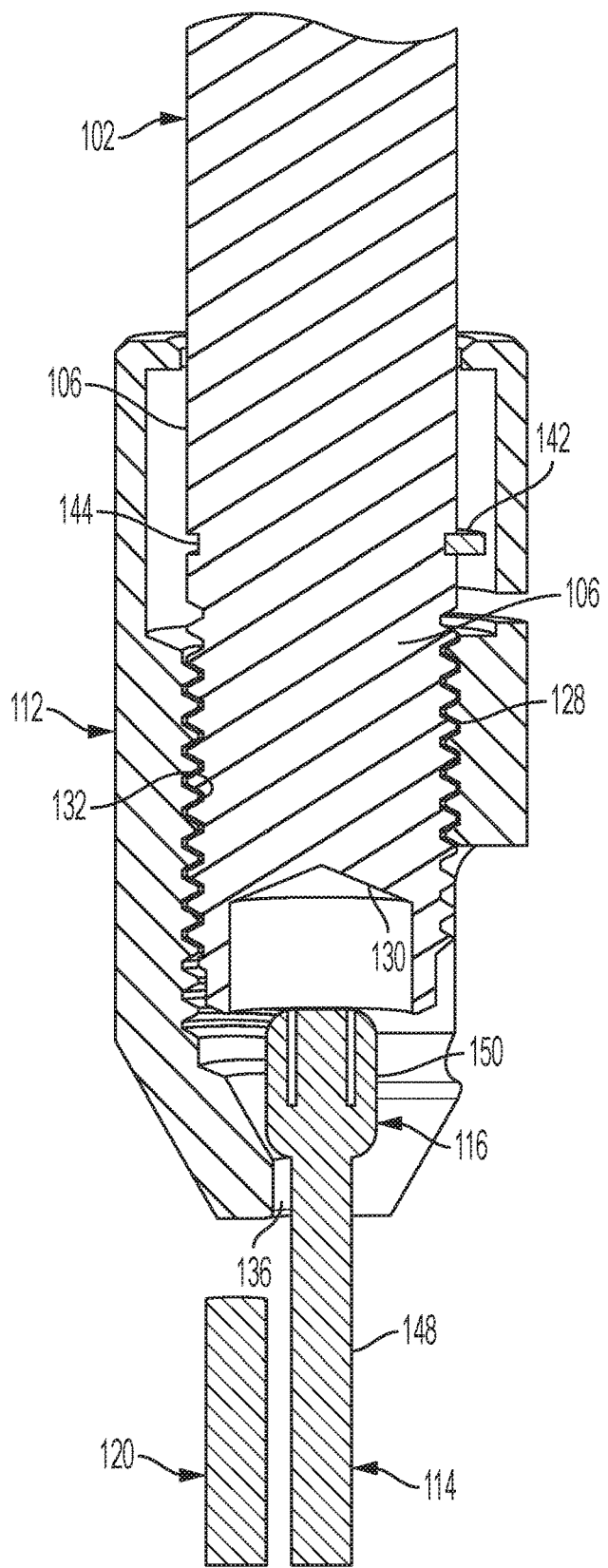
FIG. 8 is an enlarged partial cross-sectional view of a connector of the cannulated nail extractor of FIG. 1 engaged with a proximal end of an engagement wire.

The extractor 102 is configured as best shown in FIGS. 1, 4, 5 and 8. The proximal end 104 of the extractor is provided with a fastener 124, e.g., threads for attachment to a suitable extraction device. Alternatively, or in addition to threads 124, the proximal end of the extractor can have radially projecting structure 126 for connecting or aiding in connecting the extractor to a suitable extraction device. The extractor has an elongated body and a fastener 128, e.g., threads, provided at its distal end 106 for attachment to the connector 112. The extractor also includes a recessed seat 130 (FIG. 8) for engaging or nesting with the enlarged proximal end 116 of the engagement wire 114. In an exemplary aspect, the recessed seat is distally facing countersunk recess. As shown in FIG. 8, the enlarged proximal end is nested with the extractor 102, specifically the proximal end is nested within the recessed seat.

Figure 7:
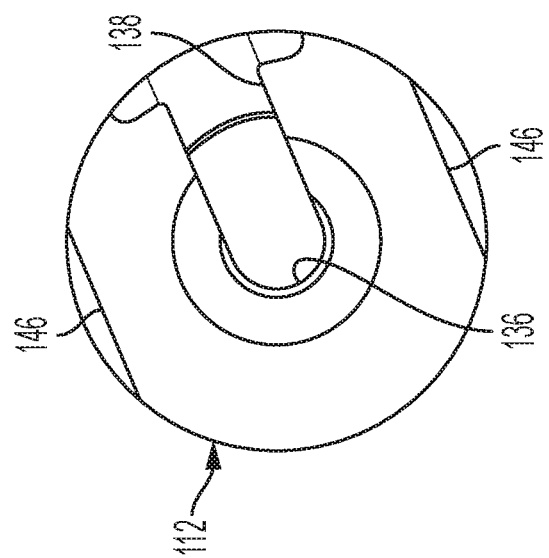
FIG. 7 is an enlarged bottom view of the connector of FIG. 6.

FIGS. 6-9 show the construction of the connector 112 which is formed as a substantially hollow bullet-shaped connector having a tapered frustoconical shaped distal end. The connector 112 can be releasably connected to the extractor 102 by a cooperating fastener to the fastener 128, e.g., by cooperating threads 132 on the connector which mate with the threads on the extractor. The connector further includes a through hole 136 for the passage of the engagement wire therethrough. In addition, as shown in FIG. 7, the connector 112 includes a lateral slot 138 for the passage of the engagement wire laterally therethrough. The connector further includes a transverse slot 140 (FIGS. 6 and 9) configured to receive a spring clamp 142 for releasably securing the connector to the extractor 102 via an annular notch 144 (FIG. 8) formed on the extractor to receive the spring clamp. The connector 112 may also include a pair of opposing flat sides 146 (FIGS. 6 and 7) for receiving a tightening and loosening tool such as a wrench or the like to firmly attach the connector to the extractor 102 and to remove the connector therefrom.

Figure 9:
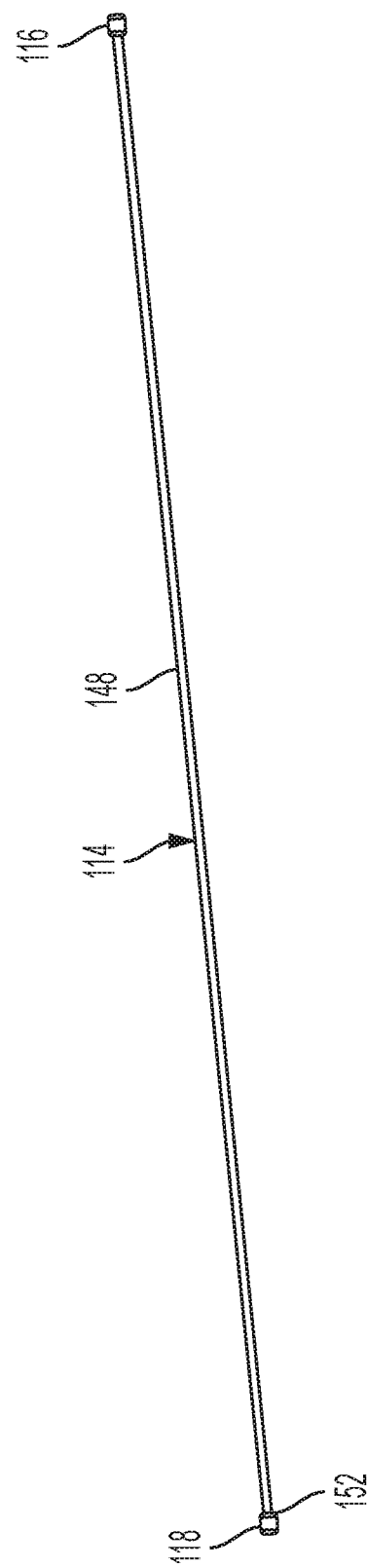
FIG. 9 is a perspective view of an engagement wire of the cannulated nail extractor of FIG. 1.

Referring to FIG. 9, the engagement wire 114 includes an elongated body 148 bounded by the enlarged proximal and distal ends 116, 118. As most clearly shown in FIG. 9, the enlarged distal end 118 of the engagement wire has a diameter larger than a diameter of the engagement wire body 148. The enlarged, substantially bulbous-like proximal end 116 of the engagement wire 114 may be formed as a bearing 150 attachable to the distal end 106 of the extractor 102 or, alternatively, integrally formed with the wire body. Additionally, as shown in FIGS. 9 and 13, the engagement wire 114 includes at least one of a chamfer, round and/or step 152 between the wire body 148 and the enlarged distal end 118 which is configured for engagement with a distally facing end 154 of the cannulated nail 122.

Figure 10:
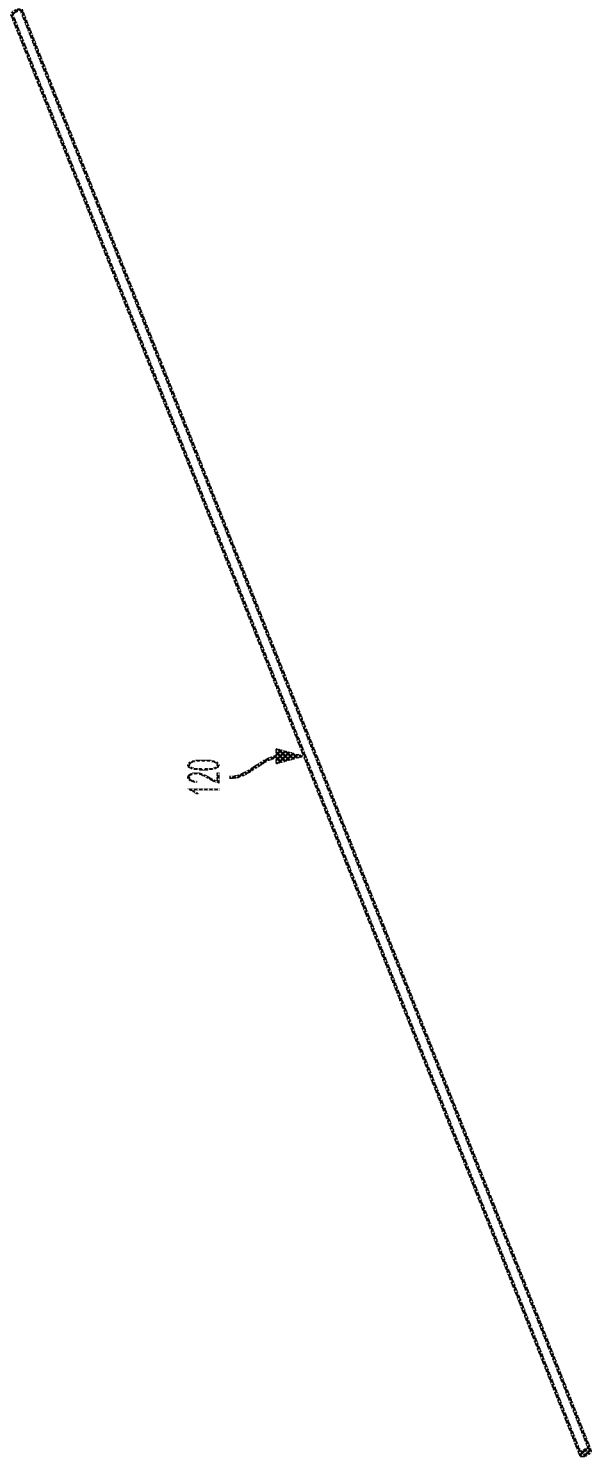
FIG. 10 is a perspective view of a positioning wire of the cannulated nail extractor of FIG. 1.

The positioning wire 120 is configured as best shown in FIG. 10. The positioning wire is an elongated wire having a constant diameter along substantially its entire length. The longitudinal cross-section of the wire is preferably circular and may alternatively be any other suitable cross-sectional shape suitable for its intended purpose.

Figure 11:
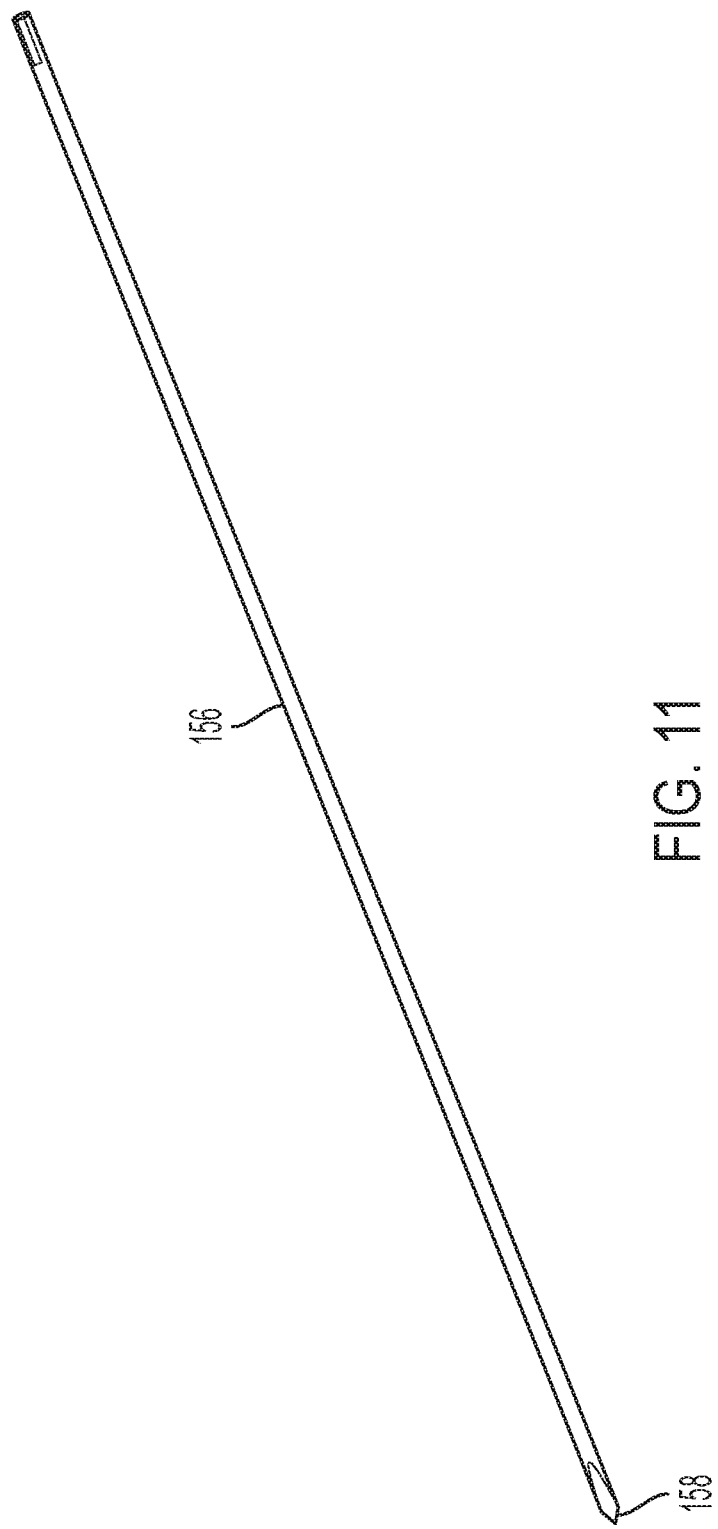
FIG. 11 is a perspective view of a cannulated nail reamer device used to clear the cannulation to allow passage of the engagement wire and positioning wires of FIGS. 9 and 10.
Figure 12:
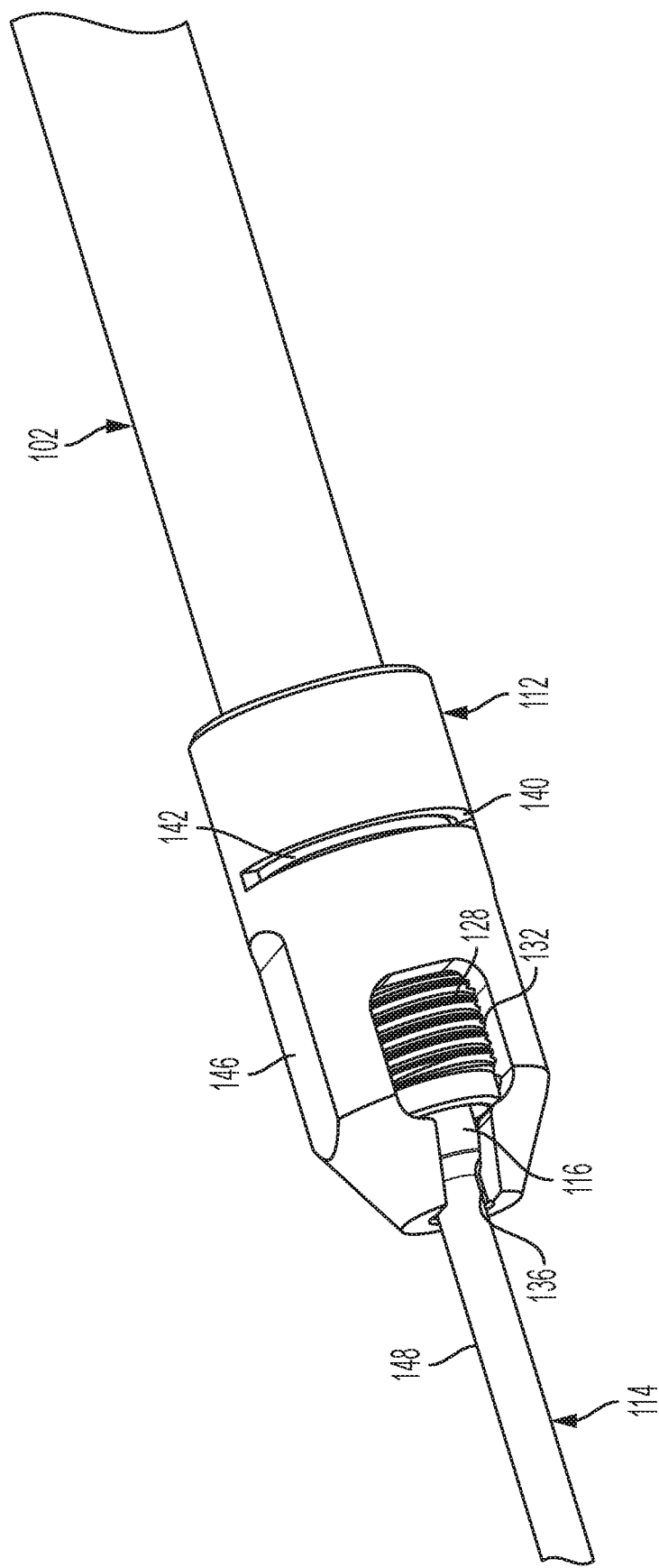
FIG. 12 is an enlarged assembled view of a central portion of the cannulated nail extractor of FIG. 1.

FIG. 11 shows a reamer device 156 used to clear the cannulation of the cannulated nail 122 of bone marrow and any other matter present in the cannulated nail that might prevent passage of the engagement wire 114 and positioning wire 120 through the cannulated nail. The reamer device 156 is constructed as an elongated rod having a pointed distal end 158 which may be inserted and rotated in the cannulation to ream out matter present in the cannulated nail and past the distally facing end 154 of the cannulated nail. Once the cannulation is cleared of matter by the reamer device, the engagement wire and positioning wire may be inserted into the cannulation as described below.

Figure 13:
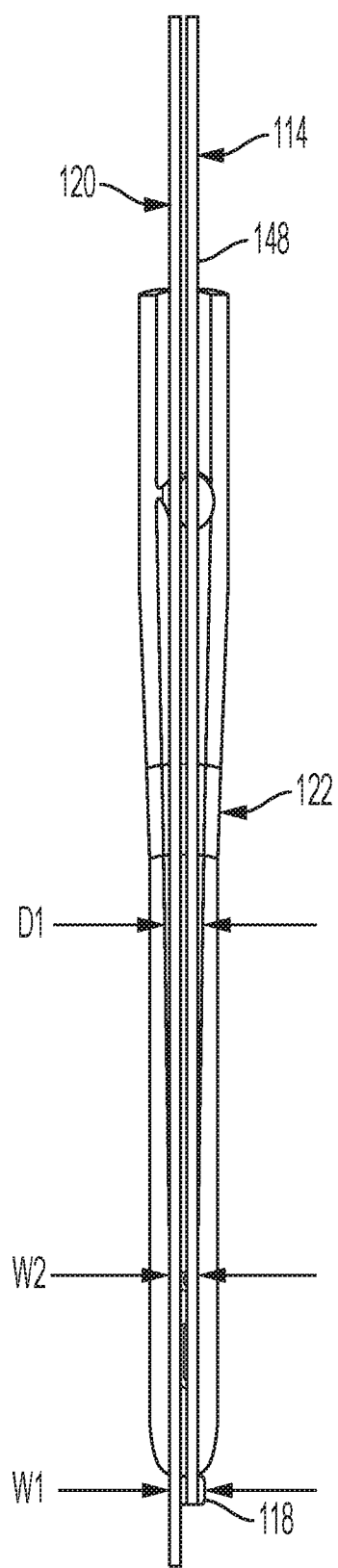
FIG. 13 is an enlarged partial elevational cross-sectional view of a cannulated nail with the engagement wire and positioning wire of the cannulated nail extractor of FIG. 1 inserted therein.
Figure 14:
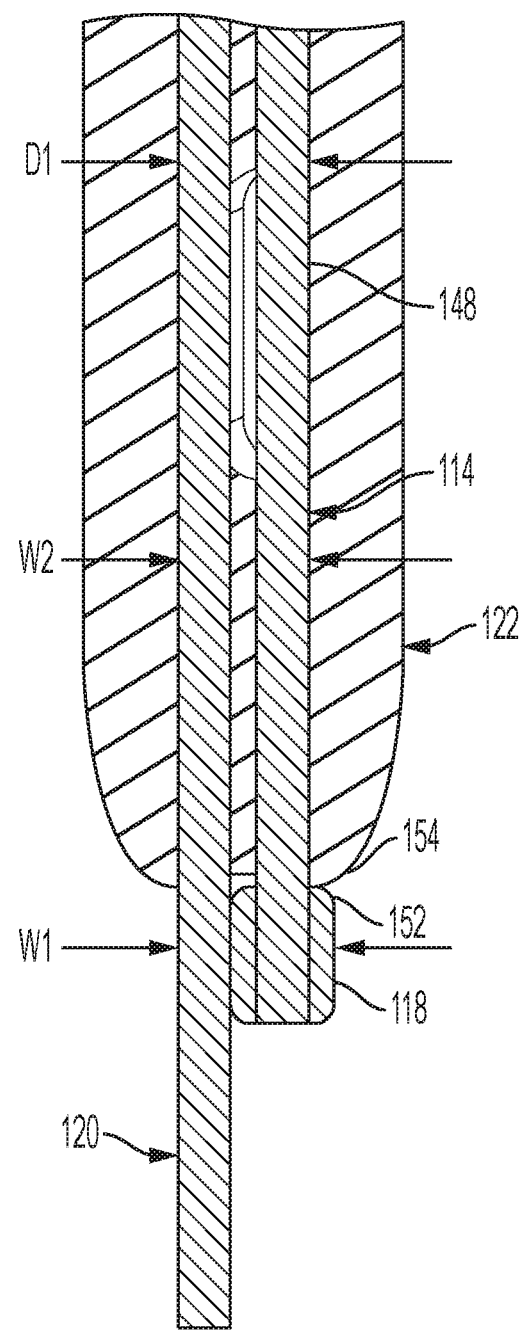
FIG. 14 is an enlarged partial elevational cross-sectional view of the distal end of a cannulated nail with the engagement wire and positioning wire of the cannulated nail extractor of FIG. 1 inserted therein.

As shown in FIGS. 13 and 14, an overall combined width W1 of the positioning wire 120 and enlarged distal end 118 of the engagement wire 114 is sufficiently larger than an overall inside diameter D1 of the cannulated nail 122 such that the overall combined width W1 of the positioning wire and enlarged distal end of the engagement wire cannot pass through the cannulated nail. Further, the overall combined width W2 of the positioning wire 120 and a main wire body 148 of the engagement wire 114 is sufficiently smaller than an overall inside diameter D1 of the cannulated nail 122 such that the overall combined width of the positioning wire and the main wire body of the engagement wire can pass through the cannulated nail. Moreover, as shown in FIGS. 1-3, 13 and 14, an overall length of the engagement wire 114 and positioning wire 120 is sufficient to pass through an entirety of the cannulated nail 122.

Referring to FIGS. 5-8, assembly of the cannulated nail extractor 100 may be achieved as follows. First, a user grasps the engagement wire 114 and inserts the enlarged proximal end 116 thereof through the lateral slot 138 in the connector 112 whereby the body 148 of the engagement wire projects through the connector through hole 136. Then, the user inserts the distal end 106 of the extractor 102 into the open proximal end of the connector until the fastener 128, e.g., threads of the extractor come into contact with the cooperating fastener 132, e.g., threads of the connector. Thereafter, the fasteners 128 and 132 are tightened, e.g., by turning the connector about the extractor or by turning the extractor within the connector until the bearing 150 at the enlarged proximal end of the engagement wire becomes nested in the recessed seat 130 of the extractor. A wrench or similar turning tool can then be engaged with the opposing flat sides 146 of the connector to further tighten the connector onto the extractor. In order to securely retain the extractor onto the connector, the spring clamp 142 is inserted through the transverse slot 140 of the connector and brought into engagement with notch 144 provided in the extractor. At this point, a device such as a T-handle 108 (FIG. 2), a C-frame 110 (FIG. 3) or other suitable extraction device may be attached to the proximal end 104 of the extractor as described above. With the cannulated nail extractor so constructed, the engagement wire 114 and positioning wire 120 of the cannulated nail extractor may be inserted through a cannulated nail 122 and used to extract the cannulated nail from a bone in the manner described below.

The subject disclosure also provides a method for extracting a cannulated nail using the above-described cannulated nail extractor 100. The method comprises, after reaming of the cannulated nail 122 by the reamer device 156, inserting the engagement wire 114 through the cannulated nail until the enlarged distal end 118 passes through a bottom of the cannulated nail (FIG. 13). The method further comprises inserting the positioning wire 120 through the cannulated nail until a distal end of the positioning wire passes through the bottom of the cannulated nail and urges the enlarged distal end 118 of the engagement wire 114 into engagement with a distally facing end 154 (FIG. 14) of the cannulated nail. The method further comprises exerting an extraction force on the extractor 102 (by either of the extraction devices 108, 110 of FIGS. 2 and 3 or any other suitable extraction device) to produce extraction force by engagement of the enlarged distal end 118 of the engagement wire 114 on the distally facing end 154 of the cannulated nail.

It will be appreciated by those skilled in the art that changes could be made to the exemplary embodiments described above without departing from the broad inventive concept thereof. It is to be understood, therefore, that this disclosure is not limited to the particular embodiments disclosed, but it is intended to cover modifications within the spirit and scope of the subject disclosure as defined by the appended claims.

I claim:

1. A cannulated nail extractor comprising:
  an extractor that includes:
    a proximal end for connecting to a device, and
    a distal end opposite the proximal end;
  a connector extending from the distal end of the extractor, wherein the connector includes a transverse slot through a lateral wall of the connector configured to receive a spring clamp for releasably securing the connector to extractor;
  an engagement wire having an enlarged proximal end configured to engage the extractor and an enlarged distal end; and
  a positioning wire for insertion into a cannulated nail.

2. The cannulated nail extractor of claim 1, wherein the extractor includes an elongated body.

3. The cannulated nail extractor of claim 1, wherein the extractor includes a recessed seat for engaging the enlarged proximal end of the engagement wire.

4. The cannulated nail extractor of claim 1, wherein the enlarged proximal end is nested with the extractor.

5. The cannulated nail extractor of claim 1, wherein the connector is threadedly connected to the extractor, or releasably connected to the extractor.

6. The cannulated nail extractor of claim 1, wherein the connector includes a through hole for the passage of the engagement wire therethrough.

7. The cannulated nail extractor of claim 1, wherein the connector includes a lateral slot for the passage of the engagement wire therethrough.

8. The cannulated nail extractor of claim 1, further comprising a spring clamp securing the connector to extractor.

9. The cannulated nail extractor of claim 1, wherein the connector includes a pair of opposing flat sides.

10. The cannulated nail extractor of claim 1, wherein the enlarged proximal end of the engagement wire is substantially bulbous.

11. The cannulated nail extractor of claim 1, wherein the enlarged proximal end of the engagement wire includes a bearing attachable to the distal end of the extractor.

12. The cannulated nail extractor of claim 1, wherein the engagement wire includes an elongated body and the enlarged distal end has a diameter larger than a diameter of the engagement wire body.

13. The cannulated nail extractor of claim 1, wherein the engagement wire includes at least one of a chamfer, round and step between a wire body of the engagement wire and the enlarged distal end.

14. The cannulated nail extractor of claim 1, wherein the positioning wire has a constant diameter along substantially its entire length.

15. The cannulated nail extractor of claim 1, wherein an overall combined width of the positioning wire and enlarged distal end of the engagement wire is sufficiently larger than an overall inside diameter of the cannulated nail such that the overall combined width of the positioning wire and enlarged distal end of the engagement wire cannot pass through the cannulated nail.

16. The cannulated nail extractor of claim 1, wherein an overall combined width of the positioning wire and a main wire body of the engagement wire is sufficiently smaller than an overall inside diameter of the cannulated nail such that the overall combined width of the positioning wire and the main wire body of the engagement wire can pass through the cannulated nail.

17. The cannulated nail extractor of claim 1, wherein an overall length of the engagement wire and positioning wire is sufficient to pass through an entirety of the cannulated nail.

18. A method for extracting a cannulated nail comprising:
using the cannulated nail extractor of claim 1, inserting the engagement wire through the cannulated nail until the enlarged distal end passes through a bottom of the cannulated nail;
inserting the positioning wire through the cannulated nail until a distal end of the positioning wire passes through the bottom of the cannulated nail and urges the enlarged distal end of the engagement wire into engagement with a distally facing end of the cannulated nail; and
exerting an extraction force on the extractor to produce extraction force by engagement of the enlarged distal end of the engagement wire on the distally facing end of the cannulated nail.

19. A cannulated nail extractor comprising:
an extractor that includes a distally facing recess at its distal end;
a connector extending from the distal end of the extractor and movable relative to the extractor;
an engagement wire having:
a bulbous proximal end configured to engage the extractor, and
an enlarged distal end; and
a positioning wire for insertion into the cannulated nail;
wherein the distally facing recess of the extractor is sized sufficiently to receive the bulbous proximal end of the engagement wire.

20. The cannulated nail extractor of claim 19, wherein the connector includes a through hole for the passage of the engagement wire therethrough and a lateral slot extending to and in communication with the through hole.

21. A cannulated nail extractor comprising:
an extractor that includes a plurality of threads adjacent to a bottom surface of the extractor at its distal end;
a connector threadedly connected to the plurality of threads at the distal end of the extractor and movable relative to the extractor;
an engagement wire having:
a bulbous proximal end configured to engage the extractor, and
an enlarged distal end; and
a positioning wire for insertion into the cannulated nail.

22. A cannulated nail extractor comprising:
an extractor that includes:
an elongated body,
a proximal end for connecting to a device,
a distal end opposite the proximal end and adjacent a bottom surface of the extractor, and
a midportion extending between the proximal end and the distal end;
a connector connected to the distal end adjacent a bottom end of the extractor;
an engagement wire having an enlarged proximal end configured to engage the extractor and an enlarged distal end; and
a positioning wire for insertion into a cannulated nail.

23. The cannulated nail extractor of claim 22, wherein the extractor includes a recessed seat for engaging the enlarged proximal end of the engagement wire.

24. The cannulated nail extractor of claim 22, wherein the enlarged proximal end of the engagement wire is nested with the extractor.

25. The cannulated nail extractor of claim 22, wherein the connector is threadedly connected to the extractor, or releasably connected to the extractor.

26. The cannulated nail extractor of claim 22, wherein the connector includes a through hole for the passage of the engagement wire therethrough, or a lateral slot for the passage of the engagement wire therethrough.

27. The cannulated nail extractor of claim 22, wherein the connector includes a pair of opposing flat sides.

28. The cannulated nail extractor of claim 22, wherein the enlarged proximal end of the engagement wire is substantially bulbous.

29. The cannulated nail extractor of claim 22, wherein the enlarged proximal end of the engagement wire includes a bearing attachable to the distal end of the extractor.

30. The cannulated nail extractor of claim 22, wherein the engagement wire includes an elongated body and the enlarged distal end has a diameter larger than a diameter of the engagement wire body.

31. The cannulated nail extractor of claim 22, wherein the engagement wire includes at least one of a chamfer, round and step between a wire body of the engagement wire and the enlarged distal end.

32. The cannulated nail extractor of claim 22, wherein an overall combined width of the positioning wire and enlarged distal end of the engagement wire is sufficiently larger than an overall inside diameter of the cannulated nail such that the overall combined width of the positioning wire and enlarged distal end of the engagement wire cannot pass through the cannulated nail.

33. The cannulated nail extractor of claim 22, wherein an overall combined width of the positioning wire and a main wire body of the engagement wire is sufficiently smaller than an overall inside diameter of the cannulated nail such that the overall combined width of the positioning wire and the main wire body of the engagement wire can pass through the cannulated nail.

34. A method for extracting a cannulated nail comprising:
using the cannulated nail extractor of claim 22, inserting the engagement wire through the cannulated nail until the enlarged distal end passes through a bottom of the cannulated nail;
inserting the positioning wire through the cannulated nail until a distal end of the positioning wire passes through the bottom of the cannulated nail and urges the enlarged distal end of the engagement wire into engagement with a distally facing end of the cannulated nail; and
exerting an extraction force on the extractor to produce extraction force by engagement of the enlarged distal end of the engagement wire on the distally facing end of the cannulated nail.

\* \* \* \* \*